(12) United States Patent
Tawil (10) Patent No.: US 12,232,492 B2
(45) Date of Patent: Feb. 25, 2025

(54) DISINFECTION OF BACTERIOPHAGES PRODUCTS USING SUPERCRITICAL CARBON DIOXIDE

(71) Applicant: PHAGELUX CANADA INC., Montreal (CA)

(72) Inventor: Nancy Tawil, Cantley (CA)

(73) Assignee: PRECISIONBIOTIX TECHNOLOGIES INC., Dover, DE (US)

( * ) Notice: Subject to any disclaimer, the term of this patent is extended or adjusted under 35 U.S.C. 154(b) by 739 days.

(21) Appl. No.: 17/050,727

(22) PCT Filed: Jun. 18, 2020

(86) PCT No.: PCT/IB2020/055749
§ 371 (c)(1),
(2) Date: Oct. 26, 2020

(87) PCT Pub. No.: WO2020/255041
PCT Pub. Date: Dec. 24, 2020

(65) Prior Publication Data
US 2023/0113410 A1  Apr. 13, 2023

Related U.S. Application Data

(60) Provisional application No. 62/864,204, filed on Jun. 20, 2019.

(51) Int. Cl.
| | | |
|---|---|---|
| A01N 25/28 | (2006.01) | |
| A01N 25/10 | (2006.01) | |
| A01N 59/04 | (2006.01) | |
| A01N 63/40 | (2020.01) | |
| A01P 1/00 | (2006.01) | |

(52) U.S. Cl.
CPC ............ *A01N 25/28* (2013.01); *A01N 25/10* (2013.01); *A01N 59/04* (2013.01); *A01N 63/40* (2020.01); *A01P 1/00* (2021.08)

(58) Field of Classification Search
CPC ........ A01N 25/28; A01N 25/10; A01N 59/04; A01N 63/40; A01P 1/00
See application file for complete search history.

(56) References Cited

U.S. PATENT DOCUMENTS

| | | | |
|---|---|---|---|
| 5,667,835 A | 9/1997 | Osajima et al. | |
| 5,723,012 A | 3/1998 | Fages et al. | |
| 10,849,944 B2 | 12/2020 | Tawil | |
| 2006/0177416 A1* | 8/2006 | Turnell ................... | A61P 27/02 514/44 R |
| 2006/0292031 A1 | 12/2006 | Chiu et al. | |
| 2016/0279070 A1 | 9/2016 | Gorecka et al. | |
| 2021/0112816 A1 | 4/2021 | Tawil | |

OTHER PUBLICATIONS

Puapermpoonsiri et al. (Eur. J. Pharm. Biopharm.,2009, vol. 72, pp. 26-33) (Year: 2009).*
Soares GC, Learmonth DA, Vallejo MC, Davila SP, González P, Sousa RA, Oliveira AL. Supercritical CO2 technology: The next standard sterilization technique?, Jan. 2019, Mater Sci Eng C Mater Biol Appl. 99:520-540.
Masamichi Kamihira et al., "Sterilization of Microorganisms with Supercritical Carbon Dioxide" Fev 1987, Agricultural and Biological Chemistry, vol. 51, Issue 2, pp. 407-412.
Written Opinion of the International Searching Authority issued by the World Intellectual Property Organization on Oct. 14, 2020 for PCT application PCT/IB2017/053744 from which the present application is a national phase.
International Search Report issued by the World Intellectual Property Organization on Oct. 14, 2020 for PCT application PCT/IB2017/053744 from which the present application is a national phase.
Vo, Huy Thanh et al., "Inactivation effect of pressurized carbon dioxide on bacteriophage Qβ and ΦX174 as a novel disinfectant for water treatment", Jun. 2014, Journal of Environmental Sciences, vol. 26, Issue 6, pp. 1301-1306.
Bernhard, A. et al., "Improved Sterilization of Sensitive Biomaterials with Supercritical Carbon Dioxide at Low Temperature", Published online Jun. 2015, PLoS One. 2015; 10(6): e0129205, pp. 1-19.
Vo, Huy Thanh et al., "Disinfection Using Pressurized Carbon Dioxide Microbubbles to Inactivate *Escherichia coli*, Bacteriophage MS2 and T4", Dec. 2013, Journal of Water and Environment Technology vol. 11(No. 6):497-505.
Schwan, William R et al., "A comparison of Selas and membrane filters for the sterilization of bacteriophage preparations", Sep. 1986, Journal of Virological Methods, vol. 14, Issue 2, , pp. 189-191.
Jul. 1998, Fages, J et al., "Viral inactivation of human bone tissue using supercritical fluid extraction", Asaio J; 44 (4):289-93.

* cited by examiner

*Primary Examiner* — Snigdha Maewall (57) ABSTRACT

There is proposed a method for the sterilization of products containing bacteriophages in a manner that will allow the bacteriophages to retain their activity and infectivity. Products containing bacteriophages are exposed to supercritical $CO_2$ under conditions causing little or no damage to structural integrity of the bacteriophages or to the structural properties of biodegradable scaffolds containing the bacteriophages.

20 Claims, 4 Drawing Sheets

DISINFECTION OF BACTERIOPHAGES PRODUCTS USING SUPERCRITICAL CARBON DIOXIDE

FIELD OF THE INVENTION

The present invention relates to the general field of bacteriophages and is more particularly concerned with the disinfection of bacteriophages products using supercritical carbon dioxide and of corresponding disinfected bacteriophages products.

BACKGROUND

Antibacterial products utilizing bacteriophages, endolysins and other biological solutions offer an alternative to antibiotics to fight undesirable bacteria, for example to target antibiotic resistant bacteria (AMR). In many applications, it may be advantageous to deliver bacteriophages using an appropriate delivery system. These delivery systems utilizing a unique suit-to-purpose technology that allow for the controlled release of bacteriophages need to be finally sterilized for many applications, such as in medical treatment of humans and animals. In some cases, the bacteriophages are embedded or otherwise associated with a bioresorbable polymer. As the polymer is degraded in-vivo, the bacteriophages can be released at a controlled rate.

Microbial decontamination is important for the manufacture of pharmaceutical and medical device products. Sterilization of medical devices containing bacteriophages poses especially a challenge to existing medical sterilization techniques as both polymers and bacteriophages are sensitive to heat and susceptible to degradation and inactivation. Bacteriophages cannot therefore typically be sterilized effectively using common sterilization processes without a significant reduction in activity.

Therefore, there is a need to provide novel and improved methods and devices for disinfecting bacteriophage containing products.

SUMMARY OF THE INVENTION

In a broad aspect, there is provided a method for producing a disinfected product including bioactive bacteriophages infectious for predetermined bacteria, the disinfected product being usable in a target environment, the method comprising: providing an initial product in which the bioactive bacteriophages are present in an initial quantity; and contacting the initial product with a disinfection fluid for a disinfection duration under disinfection conditions to produce the disinfected product from the initial product, the disinfection fluid including supercritical carbon dioxide ($scCO_2$); wherein the bioactive bacteriophages are present in a final quantity in the disinfected product, the final quantity being effective for producing lysis of the predetermined bacteria to reduce bacterial content in the target environment when the disinfected product is used in the target environment.

There may also be provided a method wherein the disinfected product is essentially free of bacterial contamination.

There may also be provided a method wherein the disinfected product is essentially free of microorganisms.

There may also be provided a method wherein providing the initial product in which the bioactive bacteriophages are present in the initial quantity includes protecting at least partially the bioactive bacteriophages from degradation by $scCO_2$.

There may also be provided a method wherein protecting the bioactive bacteriophages includes lyophilizing the bioactive bacteriophages.

There may also be provided a method wherein protecting the bioactive bacteriophages includes encapsulating the bioactive bacteriophages in microcapsules.

There may also be provided a method wherein the microcapsules encapsulate the bioactive bacteriophages inside an hydrophobic layer.

There may also be provided a method wherein the microcapsules encapsulate the bioactive bacteriophages inside a polymer.

There may also be provided a method wherein protecting the bioactive bacteriophages includes dispersing the bioactive bacteriophages inside a layer of polymer.

There may also be provided a method wherein protecting the bioactive bacteriophages includes immobilizing the bioactive bacteriophages on a polymer.

There may also be provided a method wherein protecting the bioactive bacteriophages includes adsorbing the bioactive bacteriophages on the polymer.

There may also be provided a method wherein the polymer layer is hydrophobic.

There may also be provided a method wherein the polymer is selected from (1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond, (4) a poly (ester amide urethane) wherein at least one diol, at least one diacid, and at least one amino acid are linked together through an ester bond, an amide bond, and a urethane bond,

(5) a poly (ester urea) wherein at least one diol and at least one amino acid are linked together through an ester bond and a urea bond, and (6) a poly (ester urethane) wherein at least one diol and at least one amino acid are linked together through an ester bond and a urethane bond, further wherein the at least one diol is a compound of formula:

HO—$R_1$—OH, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene, the at least one diacid is a compound of formula:
HO—(CO)—$R_3$—(CO)—OH, $R_3$ is $C_2$-$C_{12}$ alkylene,
the at least one amino acid is chosen from naturally occurring amino acids and non-naturally occurring amino acid.

There may also be provided a method The method as defined in claim 13, wherein the polymer is a poly (ester amide urea) comprising the following two blocks with random distribution thereof:

wherein
the ratio of l:m ranges from 0.05:0.95 to 0.95:0.05, l+m=1,
$R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes, $R_3$ is $C_2$-$C_{12}$ alkylene,
$R_2$ and $R_4$ are independently chosen from the side chains of L- and D-amino acids so that the carbon to which $R_2$ or $R_4$ is attached has L or D chirality.

There may also be provided a method wherein $R_1$ is —$(CH_2)_6$—, $R_3$ is —$(CH_2)_8$— and both $R_2$ and $R_4$ are the side chain of L-leucine.

There may also be provided a method wherein the disinfection fluid consists essentially of $scCO_2$.

There may also be provided a method wherein the disinfection fluid includes at least 99.9% of $scCO_2$.

There may also be provided a method wherein the disinfection fluid is substantially free of water.

There may also be provided a method wherein the disinfection fluid further comprises a sterilant additive in addition to $scCO_2$.

There may also be provided a method wherein the sterilant additive is suitable for increasing $CO_2$ penetration through bacterial cellular membranes.

There may also be provided a method wherein the sterilant additive has acidic properties, oxidative properties or both acidic and oxidative properties.

There may also be provided a method wherein the sterilant additive is selected from the group consisting of acetic acid, tert-butyl hydroxy peroxide, paracetic acid, ethanol, formic acid and hydrogen peroxide.

There may also be provided a method wherein the disinfection fluid includes between about 0.2% to about 10% of the sterilant additive per volume.

There may also be provided a method wherein the disinfection fluid includes between about 0.5% to about 2% of the sterilant additive per volume.

There may also be provided a method wherein the disinfection conditions include a pressure of $scCO_2$ of between about 8 MPa and about 11 MPa.

There may also be provided a method wherein the disinfection conditions include a pressure of $scCO_2$ between about 8 MPa and about 21 MPa.

There may also be provided a method wherein the disinfection conditions include a pressure of $scCO_2$ of between about 9 MPa and about 10 MPa.

There may also be provided a method wherein the disinfection conditions include exposition to the disinfection fluid at a temperature of between about 31° C. and about 38° C.

There may also be provided a method wherein the disinfection conditions include exposition to the disinfection fluid at a temperature of between about 31° C. and about 50° C.

There may also be provided a method wherein the disinfection duration is between about 30 min to about 120 min.

There may also be provided a method wherein the method reduces a phage titre of the bioactive bacteriophage in a bacteriophage containing portion of the initial product by at most a factor of 100 so that the final quantity is at least 1 percent of the initial quantity.

There may also be provided a method wherein the method reduces the phage titre of the bioactive bacteriophage in a bacteriophage containing portion of the initial product by at most a factor of 10 so that the final quantity is at least 10 percent of the initial quantity.

In another broad aspect, there is provided a method of eliminating or reducing bacterial contamination of a product including a bacteriophage containing composition, the method comprising exposing the product to supercritical $CO_2$ ($scCO_2$), wherein the bacteriophage containing composition includes bioactive bacteriophages after exposition to $scCO_2$.

There may also be provided a method wherein the bacteriophage containing composition includes bacteriophages in solution.

There may also be provided a method wherein the bacteriophage containing composition includes lyophilized bacteriophages.

There may also be provided a method wherein the bacteriophage containing composition includes bacteriophages dispersed in a polymer.

There may also be provided a method wherein the bacteriophage containing composition includes bacteriophages immobilized on a polymer.

There may also be provided a method wherein the bacteriophage containing composition includes bacteriophages adsorbed, adhered or otherwise immobilized on a surface.

There may also be provided a method wherein the product is an implant for implantation in a human or animal body, the surface being an exposed surface of the implant.

There may also be provided a method wherein the bacteriophage containing composition is treated with a sterilant additive in addition to $scCO_2$.

There may also be provided a method wherein the bacteriophage containing composition is treated with the sterilant additive simultaneously with the $scCO_2$.

There may also be provided a method wherein the sterilant additive is suitable for increasing $CO_2$ penetration through bacterial cellular membranes.

There may also be provided a method wherein the sterilant additive has acidic properties, oxidative properties or both acidic and oxidative properties.

There may also be provided a method wherein the sterilant additive is selected from the group consisting of acetic acid, tert-butyl hydroxy peroxide, paracetic acid, ethanol, formic acid and hydrogen peroxide.

There may also be provided a method wherein the bacteriophage containing composition is treated with $scCO_2$ at between about 9 MPa and about 10 MPa.

There may also be provided a method wherein the bacteriophage containing composition is treated with $scCO_2$ at between about 31° C. and about 38° C.

There may also be provided a method wherein the predetermined duration is between about 30 min and about 120 min.

In another broad aspect, there is also provided a disinfected product obtained any of the above-described methods and combinations thereof, the disinfected product being usable in a target environment for controlling growth of predetermined bacteria in the target environment, the disinfected product comprising: bioactive bacteriophages infectious for the predetermined bacteria.

There may also be provided a disinfected product wherein the disinfected product is essentially free of bacterial contamination.

There may also be provided a disinfected product wherein the disinfected product is selected from the group consisting of a polymer patch, a suspension of polymer microcapsules, an implant including a surface coated with a polymer and a powder composition including lyophilized bacteriophages.

In yet another broad aspect, there is provided a method of controlling growth of predetermined bacteria in a target environment using bioactive bacteriophages infectious for the predetermined bacteria, the method comprising: contacting the disinfected product described above with the predetermined bacteria in the target environment and producing lysis of the predetermined bacteria with the bioactive bacteriophages.

Advantageously, the proposed method can eliminate or essentially eliminate unwanted microorganisms in a product or part of a product while preserving enough bacteriophage activity to fight the bacteria that are targeted by the bacteriophages.

In other embodiments, the proposed methods are performed with near supercritical $CO_2$, that is $CO_2$ that is at slightly below the critical temperature, the critical pressure or both the critical temperatures and pressures. For example, in the above-mentioned temperature intervals, the lower temperatures may be changed from 31° C. to 30° C. Also, the pressure may be bounded at the lower end at about 7 MPa, instead of 8 or 9 MPa. In such embodiments, this near-supercritical $CO_2$ may be used instead of supercritical $CO_2$ in all the claims and embodiments/variants described herein.

Other objects, advantages and features of the present invention will become more apparent upon reading of the following non-restrictive description of preferred embodiments thereof, given by way of example only with reference to the accompanying drawings.

DETAILED DESCRIPTION

A fluid is under supercritical conditions when it is at a pressure (P) and temperature (T) above those of the fluid's critical point (Pc, Tc). The proposed sterilization process consists of pumping $CO_2$ into a high-pressure cell containing the material to be treated for the selected pressure, temperature, and duration of the process. Optionally, the setup can be equipped with an additional pump for injection of a sterilant additive with acidic/oxidative properties that may improve $CO_2$ penetration through bacterial cellular membranes (e.g. acetic acid, tert-butyl hydroxy peroxide, paracetic acid, ethanol, formic acid and hydrogen peroxide).

Supercritical conditions of $CO_2$ are achieved at mild pressures (Pc=7.39 MPa) and temperatures (Tc=31.1° C.), amenable to bacteriophages. Moreover, the low reactivity of supercritical (sc) $CO_2$ does not cause significant formation of free radicals and reactive species, which may otherwise alter the structural and mechanical properties of the scaffold and the bacteriophages. Treatment time is short enough to be practical, with studies ranging from 5 min to 100 h.

A non-binding proposed mechanism of action of $scCO_2$ resides in the acidification of the bacterial cytoplasm. This requires that $CO_2$ is allowed to dissolve in the aqueous medium containing the microorganisms and transforms into carbonic acid form, which in turn dissociates into bicarbonate and hydrogen ions. This has the effect of lowering the pH and damages the cell membrane structure resulting in an increase in permeability that facilitates further penetration of $CO_2$ (Ribiero et al., 2019). The penetration and accumulation of $CO_2$ in the cells allow for interference with the cell metabolism, also contributing to the sterilization efficacy, by inducing carbonate salt precipitation through inactivation of decarboxylase enzymes by inducing carbonate salt precipitation, increased extraction of lipids from the double layer of phospholipids from the cell membranes and also from intracellular structures.

The use of supercritical $CO_2$ ($scCO_2$) was disclosed as an alternative to existing sterilization technologies for a wide range of products. Specifically, these disclosures pertain to techniques where vegetative bacteria, spore-forming bacteria, fungi, yeast, and viruses are inactivated. For bacteriophage products, it is important to highlight the difference between sterilization and disinfection, the latter term referring to the selective process for the elimination of pathogenic microorganisms, and the former one referring to elimination of all microorganisms and viruses. In the case of bacteriophage products, a disinfection method is needed to inactivate detrimental bacteria, without affecting the viability and release of the bacteriophages from their enclosing matrix. In the case of viruses, their inactivation depends on their structure. The sterilization of bacteriophage-containing products using $scCO_2$ in a matter that inactivates bacteria but preserves the activity of the bacteriophages, without affecting the release properties of the matrix is novel and contrary to what is known. $CO_2$ sterilization is considered a very effective method of completely sterilizing various items, and is considered very useful as it is believed to completely eliminate all microorganisms, including viruses and bacteriophages. Surprisingly, it has been found that it is possible to protect bacteriophages from undue degradation in some products while The present invention aims to fulfill these needs using relatively mild operating pressures and temperatures and moderate processing times, for example, in combination with a protection of the bacteriophages in the product to disinfect.

Broadly speaking, there is proposed a method for producing a disinfected product including bioactive bacteriophages infectious for predetermined bacteria, the disinfected product being usable in a target environment. In some embodiments, the disinfected product is free of bacteria and, in some embodiments, of viruses and other microorganisms other than the bioactive bacteriophages. In some embodiments, the disinfected product is essentially free of bacteria and viruses, including bacteriophages, other than the bioactive bacteriophages that are willingly included in sufficient quantity in the product. Essentially free means that there may be some residual contamination in some of the samples that are processed by the proposed method, but that the proposed method satisfies known industry standards relevant to sterilization of devices intended to contact humans and animal invasively, such as during surgery or for use as bandages, among other possibilities.

Bacteriophages are bioactive if they can cause lysis in target bacteria when put in contact with such bacteria. For example, bioactive bacteriophages will cause the formation of lysis patched during standard phage titration methods. Indeed, some bacteriophages may still be present in disinfected or sterilized preparations, but in an inactive form, unable to infect bacteria. The proposed method aims at preserving enough bacteriophage activity to act against harmful bacteria when the proposed product is used, for example for the treatment of humans and animals, or in the food processing industry, among other possibilities. The bacteriophages may be all immediately available when the product is used, or may be in totality or in part released gradually by the product.

In the proposed method, an initial product in which the bioactive bacteriophages are present in an initial quantity is provided. If sterilization were not a concern, this product would be used directly for its intended purpose. However, the proposed product must satisfy sterilization criteria for safety and the proposed method is performed so that these sterilization criteria are satisfied while preserving enough activity in the bioactive bacteriophages. The method includes contacting the product with a disinfection fluid for a disinfection duration under disinfection conditions to produce the disinfected product, the disinfection fluid including supercritical carbon dioxide ($scCO_2$). The bioactive bacteriophages are present in a final quantity in the disinfected product, the final quantity being effective for producing lysis of the predetermined bacteria to reduce bacterial content in the target environment when the disinfected product is used in the target environment.

In some embodiments, the disinfected product is essentially free of bacterial contamination or essentially free of microorganisms.

In some embodiments, the bacteriophages are protected at least partially the bioactive bacteriophages from degradation by $scCO_2$. Such protection can take many forms, for example lyophilizing the bioactive bacteriophages before or after integration with the initial product, encapsulation or immobilization (for example through adsorption, physisorption, or covalent bonds) of the bioactive bacteriophages in or on polymer microcapsules, patches made of a layer of polymer or in layers of polymers coating at least part of a product including different other materials. The polymer may be hydrophobic and/or amino-acid based.

A non-limiting example of a suitable polymer is a polymer selected from (1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond,

(4) a poly (ester amide urethane) wherein at least one diol, at least one diacid, and at least one amino acid are linked together through an ester bond, an amide bond, and a urethane bond, (5) a poly (ester urea) wherein at least one diol and at least one amino acid are linked together through an ester bond and a urea bond, and (6) a poly (ester urethane) wherein at least one diol and at least one amino acid are linked together through an ester bond and a urethane bond, further wherein the at least one diol is a compound of formula:
HO—$R_1$—OH, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene, the at least one diacid is a compound of formula:
HO—(CO)—$R_3$—(CO)—OH, $R_3$ is $C_2$-$C_{12}$ alkylene,
the at least one amino acid is chosen from naturally occurring amino acids and non-naturally occurring amino acid.

In some embodiments, the polymer is selected from
(1) a poly (ester amide urea) wherein at least one diol, at least one diacid, and at least one amino acid are linked together through an ester bond, an amide bond, and a urea bond,

(2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond, and

(4) a poly (ester amide urethane) wherein at least one diol, at least one diacid, and at least one amino acid are linked together through an ester bond, an amide bond, and a urethane bond, wherein the at least one diol, at least one diacid, and at least one amino acid are as defined in the preceding paragraph.

In some more specific embodiments of the invention, the polymer is a poly (ester amide urea) comprising the following two blocks with random distribution thereof:

wherein
the ratio of l:m ranges from 0.05:0.95 to 0.95:0.05, l+m=1,
$R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes, $R_3$ is $C_2$-$C_{12}$ alkylene,
$R_2$ and $R_4$ are independently chosen from the side chains of L- and D-amino acids so that the carbon to which $R_2$ or $R_4$ is attached has L or D chirality. This polymer is referred herein as a PEAU.

In the above polymers, in some very specific embodiments of the invention, one or more of the following hold: $R_1$ is —$(CH_2)_6$—, $R_3$ is —$(CH_2)_8$—, or both $R_2$ and $R_4$ are the side chain of L-leucine. The PEAU in which these hold true is referred to herein as "the Leucine PEAU".

Blends of the above-mentioned polymers are also usable in the preparation of the compositions of the present invention. More details regarding such polymers and others usable with the present invention are provided in PCT application PCT/US2016/038527 and U.S. patent application Ser. No. 15/188,783, the contents of which is hereby incorporated by reference in its entirety. The present application claims priority from U.S. provisional patent application 62/353,658 filed Jun. 23, 2016, the contents of which is hereby incorporated by reference in its entirety.

Encapsulated bacteriophages are encapsulated in microcapsules made of a suitable polymer, such as a PEAU of the Leucine PEAU, among other possibilities. Due to both groups, ester and amide, PEAU is biodegradable (ester group) and have good thermal stability and mechanical strength (amide group with strong intermolecular interactions). The incorporation of leucine, or other suitable amino acid, improves the biocompatibility of the polymer. The biodegradation rate of this polymer can easily be adjusted by changing its exact composition and molecular weight. When microcapsules are formed, the liberation rate of any product incorporated therein can be adjusted by controlling the size and thickness of the microcapsules.

Such a polymer is synthesized, in some embodiments, by interfacial polycondensation of the monomer L6, di-p-sulfonic acid salt of bis-(L-leucine)-1,6-hexylene diester with trisphogene/sebacoyl chloride with water/dichloromethane system. The use of dichloromethane allows direct utilization of the biocomposite for bacteriophages incorporation therefore for microcapsules fabrication. This method is fast, irreversible, involves two immiscible phases at room temperature and lead to high molecular weight polymer. Synthesis of the monomer L6 may be executed in the presence of p-toluene sulfonic acid by condensation of L-leucine with 1,6-hexanediol in refluxed cyclohexane, because it is less toxic than solvents such as benzene. Purification includes recrystallization from water, filtration and drying under vacuum.

In a specific non-limiting embodiment, the microcapsules are fabricated using a water-in-oil-in-water double emulsion-solvent, where the addition of the bacteriophages occurs in some embodiments in the secondary emulsion to minimize their exposure with the solvent dichloromethane (DCM). The DCM can also be replaced by an other suitable solvent, such as ethyl acetate, chloroform, or another organic solvent.

The disinfection fluid may essentially comprises $scCO_2$, at least 99.9% of $scCO_2$, or any other suitable purity of $scCO_2$. In some embodiments, the disinfection fluid is essentially free of water. In some embodiments, disinfection fluid further comprises a sterilant additive in addition to $scCO_2$. The sterilant additive facilitates disinfection, for example by being suitable for increasing $CO_2$ penetration through bacterial cellular membranes. For example, the sterilant additive has acidic properties, oxidative properties or both acidic and oxidative properties. Non-limiting example of sterilant additives include acetic acid, tert-butyl hydroxy peroxide, paracetic acid, ethanol, formic acid and hydrogen peroxide.

It has been found that pressures of $scCO_2$ of between about 8 MPa and about 11 MPa, or of between about 9 MPa and about 10 MPa, may be particularly useful in some embodiments, although other pressures are within the scope of the present invention. Also, treatment temperatures of between about 30° C. and about 38° C. for about 30 min to about 120 min have been found to be efficient in disinfecting the product while preserving enough bacteriophage activity, but other values for these parameters may be used in alternative embodiments, for example up to about 21 MPa and about 50° C.

Disinfection should be gentle enough so that the phage titre (number of pFU in the phage-containing part of the product) is not reduced too much. While a small reduction is acceptable, reduction to a very small phage titre is undesirable. In some embodiments, the method reduces a phage titre of the bioactive bacteriophage by at most a factor of 100 or a factor of 10 so that the final quantity is at least 1 percent or 10 percent of the initial quantity. However, larger reductions may be acceptable in other embodiments, for example at most a factor of 1000.

In use, bacteriophages present in the disinfected product may come into contact with bacteria for which they are infectious, and eliminate or reduce the number of such bacteria.

Example 1: Liquid *S. aureus* Bacteriophages

*S. aureus* bacteriophages dissolved in Tris-MgCl2-NaCl (TMN) buffer and *S. aureus* bacteriophages in TMN buffer contaminated with *E. coli* at a concentration of $10^6$ CFU/mL were subjected to two supercritical $CO_2$ conditions. Treatment 1 consisted of placing the sample in a reactor vessel heated to 35° C. and equilibrated with $CO_2$ at atmospheric pressure. Stirring and agitation mechanisms for the $CO_2$ contained in the vessel were activated (675 RPM) and the vessel was pressurized to 9.9 MPa for 2 hours exposure to $scCO_2$. Following the end of treatment, the stirring was stopped, and the samples were removed from the reactor vessel. A non-treated control of each sample type, contaminated with $10^6$ CFU/mL of bacteria (positive controls) and not contaminated (negative control), were also titrated using standard plaque assay techniques. Sterility of samples were assessed by enumeration of bacterial counts by serial dilution after 14 days incubation of the sample according to USP standards. For treatment 2, treatment 1 was repeated except the exposure time to $scCO_2$ was of 6 hours. Results show a significant drop (>4 log) of bacteriophage activity, when solutions containing buffer and bacteriophages were sterilized with both treatments.

TABLE 1

Effect of $scCO_2$ sterilization on *S. aureus* bacteriophages in liquid solutions.

| Group | Treatment 1: 2 h exposure | | Treatment 2: 6 h exposure | |
|---|---|---|---|---|
| | Phage titer (PFU/mL) | Sterility | Phage titer (PFU/mL) | Sterility |
| *S. aureus* phages No bacterial challenge No $scCO_2$ treatment | $6.2 \times 10^9$ | No growth | $3.6 \times 10^9$ | No growth |
| *S. aureus* phages No bacterial challenge $scCO_2$ treated | $1.8 \times 10^6$ | No growth | $1.0 \times 10^6$ | No growth |
| *S. aureus* phages *E. coli* bacterial challenge No $scCO_2$ treatment | $3.9*10^9$ | Growth | $2.7 \times 10^9$ | Growth |
| *S. aureus* phages *E. coli* bacterial challenge $scCO_2$ treated | $2.5 \times 10^6$ | No growth | $3.1 \times 10^4$ | No growth |

Example 2: Lyophilized *S. aureus* Bacteriophages

Lyophilized *S. aureus* bacteriophages and lyophilized *S. aureus* bacteriophages contaminated with *E. coli* at a concentration of $10^6$ CFU/mL were subjected to two supercritical $CO_2$ conditions. Treatment 1 consisted of placing the lyophilized sample in a reactor vessel heated to 35° C. and equilibrated with $CO_2$ at atmospheric pressure. The stirring and agitation mechanisms were activated (675 RPM) and the vessel was pressurized to 9.9 MPa for 2 hours exposure to $scCO_2$. Following the end of treatment, the stirring was stopped, and the samples were removed from the reactor vessel. The lyophilized bacteriophages were reconstituted by adding 500 uL of sterile TMN and were vortexed prior to analysis. A non-treated control of each sample type, contaminated with $10^6$ CFU/mL of bacteria (positive controls) and not contaminated (negative control), were also titrated using standard plaque assay techniques. Sterility of samples were assessed by enumeration of bacterial counts by serial dilution after 14 days incubation of the sample according to USP standards. For treatment 2, treatment 1 was repeated except the exposure time to $scCO_2$ was of 6 hours.

TABLE 2

Effect of scCO$_2$ sterilization on lyophilized
S. aureus bacteriophages.

| | Treatment 1: 2 h exposure | | Treatment 2: 6 hour exposure | |
|---|---|---|---|---|
| Group | Phage titer (PFU/mL) | Sterility | Phage titer (PFU/mL) | Sterility |
| S. aureus lyophilized phages No bacterial challenge No scCO$_2$ treatment | $2.4 \times 10^8$ | No growth | $1 \times 10^8$ | No growth |
| S. aureus lyophilized phages No bacterial challenge scCO$_2$ treated | $1.7 \times 10^7$ | No growth | $4.3 \times 10^7$ | No growth |
| S. aureus lyophilized phages E. coli bacterial challenge No scCO$_2$ treatment | $1.9*10^9$ | Growth | $9.3 \times 10^8$ | Growth |
| S. aureus lyophilized phages E. coli bacterial challenge scCO$_2$ treated | $4.1 \times 10^8$ | No growth | $1.4 \times 10^8$ | No growth |

Example 3: S. aureus Bacteriophages Contained in a Thin Film Biodegradable Polymer S. aureus lyophilized bacteriophages were incorporated in a matrix is composed of the Leucine PEAU. These compounds contain hydrolysable ester bonds at a monomer stage, which when incorporated into the polymeric backbones are responsible for the biodegradation of the polymer. These hydrolysable ester bonds are carefully monitored to achieve sustained, controlled release, while the mechanical properties of the polymer are given by amide functions. Each patch contains in addition, on its surface, $10^6$ PFU/cm$^2$ of immobilized bacteriophages, allowing for a burst release within the first hours post-application, followed by a controlled plateau release for a few days or more days. Once in the wound, the bacteriophage particle attaches to its host cell through specific recognition of a receptor on the host surface, followed by incorporation of the bacteriophage nucleic acids into the infected cell. The bacteriophage uses the host's cellular components to replicate its genome and assembled bacteriophage particles. The host cell is finally lysed by bacteriophage proteins, releasing the progeny bacteriophages in the environment where they can in turn start the lytic cycle again. 4 cm$^2$ of non-contaminated patches and 4 cm$^2$ of contaminated with E. coli at a concentration of $10^6$ CFU/mL in Tyvek pouches, were subjected to two supercritical CO$_2$ conditions. Treatment 1 consisted of placing the Tyvek sample in a reactor vessel heated to 35° C. and equilibrated with CO$_2$ at atmospheric pressure. The stirring and agitation mechanisms were activated (675 RPM) and the vessel was pressurized to 9.9 MPa for 2 hours exposure to scCO$_2$. Following the end of treatment, the stirring was stopped, and the samples were removed from the reactor vessel. The patch was removed from the Tyvek pouches and plated on a lawn of S. aureus bacteria to determine the diameter of lysis. A non-treated control of each sample type, contaminated with $10^6$ CFU/mL of bacteria (positive controls) and not contaminated (negative control), were also placed on the same petri dish and diameter of lysis was determined. Sterility of samples were assessed by enumeration of bacterial counts by serial dilution after 4 days incubation in TSB medium. For treatment 2, treatment 1 was repeated except the exposure time to scCO$_2$ was of 6 hours. Lysis zones for both treatments demonstrate that bacteriophages retained their activity post-treatment.

The specific patches used in this example were about 0.38 mm thick. The present method is however applicable to patches having other thicknesses, for example from about 0.1 mm to about 1 mm.

In more details, formulation 9 is obtained as follows. Formulation 9 is for example used to manufacture a biodegradable wound dressing ("artificial skin") composed of the biodegradable polymer PEAU and bacteriophages. Formulation 9 is prepare using the following steps:

1. Clean and sterilize a graduated cylinder, funnel, homogenizer, and spatula
2. Set the table in a strictly horizontal position in a chemical hood
3. Put a clean patch casting assembly (a mold) on the horizontal table.
4. Place a rectangular piece of liner in the patch casting assembly.
5. Prepare the following:
   48 mL of polymer solution containing 13% PEAU w/v in DCM
   24 vials (90-100 mg/ea) of freeze-dried phages
   0.722 g of TMN mix including: 81.4% Tris-HCl; 12.4% MgSO$_4$ and 6.2% NaCl.
6. Put the freeze-dried bacteriophages and TMN solid into a cylindrical glass vessel via a glass funnel using a spatula.
7. Pour the polymer solution in the same vessel.
8. Homogenize at 100 rpm or lower while Moving the cylindrical glass vessel with the content (dry phages+ polymer solution) by hand up and down during 30 s to homogenize the mixture.
9. Pour the homogenized mixture onto the patch casting assembly. Ensure solution is evenly distributed on the casting surface.
10. Partially cover the assembly with a rectangular metallic cover in a stable environment for 2 days at room temperature to evaporate DCM, under a hood
11. Dry the patch (uncover the assembly) in vacuum oven for 6 h at 40° C.
12. Once dry, allow temperature to decrease at room temperature before removing the patch from the cast assembly.

TABLE 3

Effect of scCO$_2$ sterilization on S. aureus bacteriophages
contained in biodegradable polymer thin film.

| | Treatment 1: 2 h exposure | | Treatment 2: 6 hour exposure | |
|---|---|---|---|---|
| Group | Lysis diameter (mm × mm) | Sterility | Lysis diameter (mm × mm) | Sterility |
| PEAU patch No phages No bacterial challenge No scCO$_2$ treatment | No lysis | No growth | No lysis | No growth |
| S. aureus lyophilized phages No phages No bacterial challenge scCO$_2$ treated | No lysis | No growth | Lysis due to cross contamination (outlier) | No growth |

TABLE 3-continued

Effect of scCO$_2$ sterilization on *S. aureus* bacteriophages contained in biodegradable polymer thin film.

| Group | Treatment 1: 2 h exposure | | Treatment 2: 6 hour exposure | |
|---|---|---|---|---|
| | Lysis diameter (mm × mm) | Sterility | Lysis diameter (mm × mm) | Sterility |
| PEAU patch No phages *E. coli* bacterial challenge No scCO$_2$ treatment | No lysis | Growth | No lysis | Growth |
| *S. aureus* lyophilized phages No phages *E. coli* bacterial challenge scCO$_2$ treated | No lysis | No growth | No lysis | No growth |
| *S. aureus* lyophilized phages *S. aureus* phages No bacterial challenge No scCO$_2$ treatment | 9 × 9 | No growth | 10 × 11 | No growth |
| *S. aureus* lyophilized phages *S. aureus* phages No bacterial challenge scCO$_2$ treated | 13 × 11 | No growth | 8 × 7 | No growth |
| *S. aureus* lyophilized phages *S. aureus* phages *E. coli* bacterial challenge No scCO$_2$ treatment | 8 × 10 | Growth | 9 × 10 | Growth |
| *S. aureus* lyophilized phages *S. aureus* phages *E. coli* bacterial challenge scCO$_2$ treated | 10 × 6 | No growth | 7 × 8 | No growth |

Example 4: Effect on Release of Bacteriophages Cocktail Contained in a Thin Film Biodegradable Polymer A cocktail of *S. aureus*, *P. aeruginosa*, and *K. pneumoniae* bacteriophages was lyophilized and incorporated in a matrix composed of the Leucine PEAU. Cocktail was diluted 1/10 in sucrose 0.1M and lyophilized (the lyophilizer temperature was set at −40° C. before putting the vials, then vacuum pump was turned ON for 3 hours. Temperature was increased to 0° C. at a rate of 1° C./min. Temperature was kept stable for 18 hours before increasing it to 25° C. at rate of 0.07° C./min. Temperature was kept stable for 6 h before decreasing it to 4° C. at a rate of 1° C./min. Caps were closed using the stoppering bag before removing the vials from lyosphilizer. 24 vials of lyophilized cocktail were mixed with 44 mL of 13% PEAU in dichloromethane and 0.72 g of TMN powder using high speed homogenizer. Patches were poured in 432 cm$^2$ Teflon tray where 3M liner (ScotchPak 9741 3.5 mm) was placed. DCM was allowed to evaporate under chemical hood overnight. Patch is then dried in vacuum oven at 40° C. for 6 h. Another sheet of the liner was placed on the dry patch. Patch was then cut to 2 cm*2 cm pieces. Each piece was placed in a Tyvek pouch with a header (A3333/I73-50). Tyvek pouches were closed with a tape and labelled properly. 4 cm$^2$ of patches in Tyvek pouches were subjected to four supercritical CO$_2$ conditions according to the following table. Bacteriophage release, stability and sterility were performed according to internal standard operating procedures. Briefly, each piece of patch is cut to five pieces: 3 pieces for release (dependent triplicate)+2 pieces for sterility testing in Tryptic Soy Agar (TSB) and Fluid Thioglycollate Medium (FTM). Each piece of the patch was to be used for release was weighed and normalize to 20-25 mg. Each piece was placed in 1.5 mL tubes containing 1 mL of EMEM+10% FBS. At timepoints 0, 0.5, 1, 2, 3, 4, 5, 24 hours the patch pieces was moved, using sterile forceps to a new 1.5 mL tubes containing 1 mL of EMEM+10% FBS. The released bacteriophages were tittered according to the following procedure: 100 µL of bacterial daily culture are added to 2.5 mL of TSB top agar (30 g/L TSB+0.7% agar). The mixture is poured on a TSA plate (30 g/L TSB+15% agar) immediately after brief vortex. 10 µL of each dilution are dispensed on the bacterial layer. Plates are incubated inverted at 37° C. for 18 hours. The plaques are counted in selected dilution (with 10-100 plaques) and the bacteriophage titer is calculated according to the following equation: bacteriophage titer=number of plaques*100/dilution factor. The cumulative release is calculated using the following equation: cumulative release=Sum of bacteriophage released for 24 hours/weight of patch piece.

Figure 1:
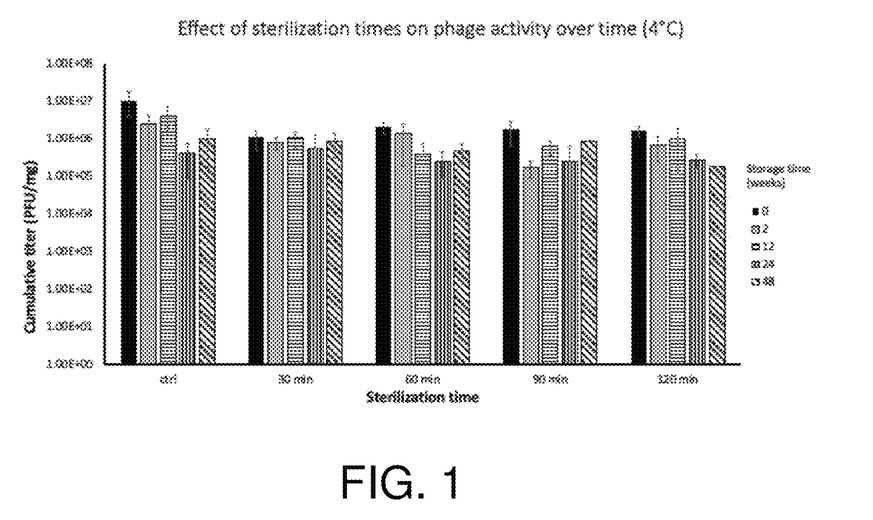
FIG. 1 illustrates cumulative release of bacteriophage cocktail after $scCO_2$ sterilization after refrigerated storage as described in example 4. Each bar group shows the titer after 0, 2, 12, 24 and 48 weeks of storage, from left to right.
Figure 2:
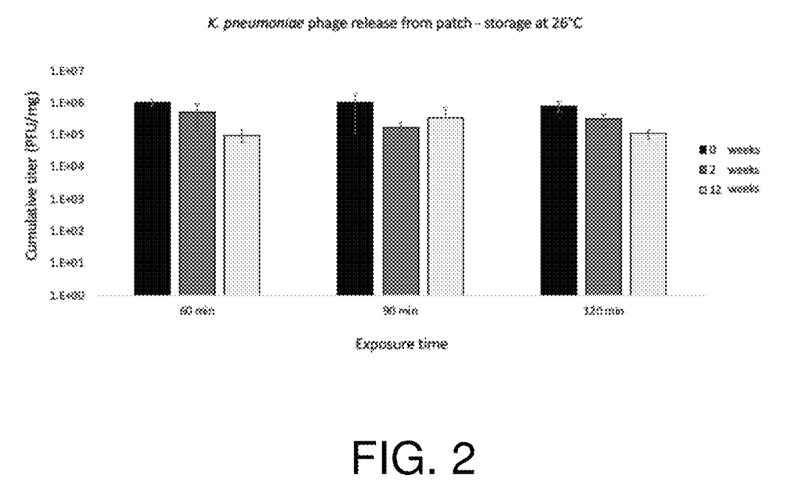
FIG. 2 illustrates cumulative release of *K. pneumoniae* bacteriophage cocktail after $scCO_2$ sterilization with accelerated stability at 26° C. as described in example 4. Each bar group shows the titer after 0, 2 and 12, weeks of storage, from left to right.

Sterility testing was performed using Trypsic Soy Broth (TSB) and Fluid Thioglycollate media (FTM) that were approved by the growth promotion test according to USP 7. Samples were incubated in 3 mL of TSB and incubate at 37° C. for 14 days and in 3 mL of FTM and incubate at 26° C. for 14 days. The samples were inspected daily for the presence of any contamination. The patch is sterile if no growth is observed in TSB and FTM after 14 days All patches remained sterile for all groups. FIG. 1 shows that the bacteriophages released was not affected for all treatments when stored at 4° C. FIG. 2 shows preliminary results obtained for *K. pneumoniae* for Treatments 2, 3, and 4 showing accelerated stability at 26° C.

TABLE 4 scCO$_2$ sterilization programs according to different exposure times

| | Treatment 1 | Treatment 2 | Treatment 3 | Treatment 4 |
|---|---|---|---|---|
| Run time | 30 minutes | 60 minutes | 90 minutes | 120 minutes |
| Pressurization/ Depressurization times | 09:50/17:28 | 13:35/18:05 | 08:59/18:05 | 06:54/29:57 |
| Target temperature | 35° C. | 35° C. | 35° C. | 35° C. |
| Target pressure | 1,436 psi | 1,436 psi | 1,436 psi | 1,436 psi |
| Stirrer speed | 675 rpm | 675 rpm | 675 rpm | 675 rpm |

Example 5: Bacteriophages Contained in Polymeric Microcapsules

Figure 3:
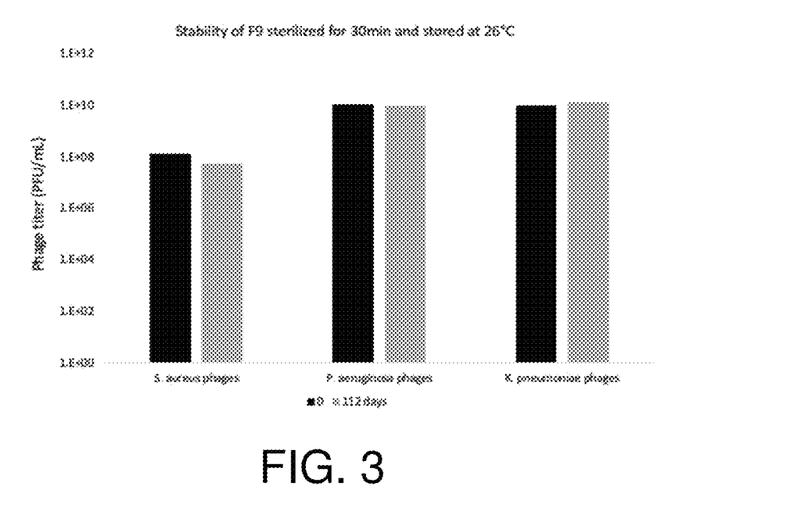
FIG. 3 illustrates accelerated stability (stored at 26° C.) for Formulation 9 sterilized for 30 minutes by $scCO_2$ as described in example 5.
Figure 4:
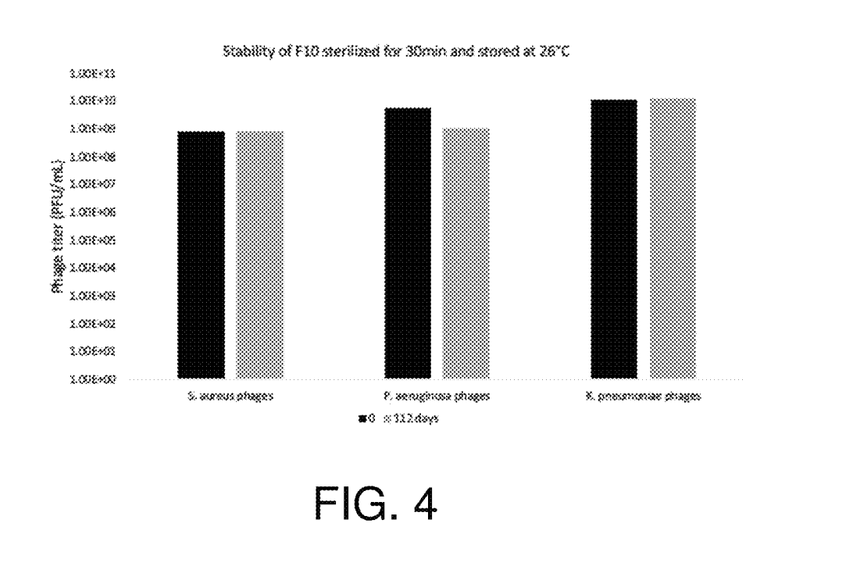
FIG. 4 illustrates accelerated stability (stored at 26° C.) for Formulation 10 sterilized for 30 minutes by $scCO_2$ as described in example 5.
Figure 5:
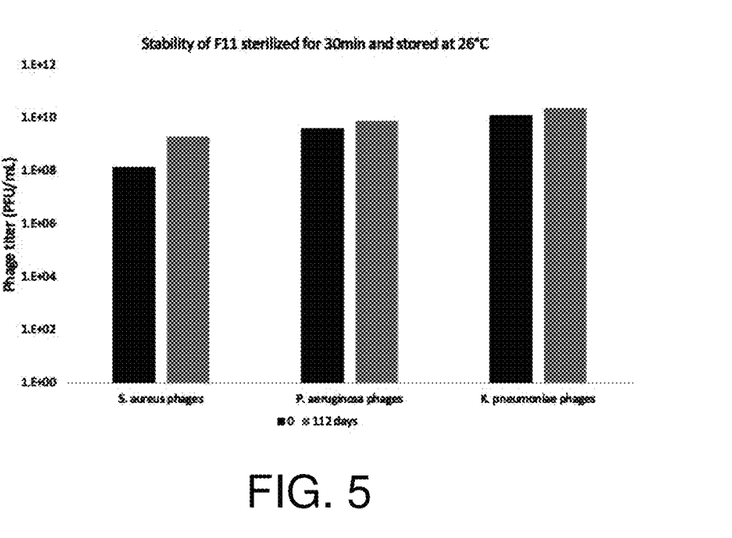
FIG. 5 illustrates accelerated stability (stored at 26° C.) for Formulation 11 sterilized for 30 minutes by $scCO_2$ as described in example 5.

A cocktail of *S. aureus*, *P. aeruginosa*, and *K. pneumoniae* bacteriophages was encapsulated into PEAU Microencapsulation was achieved by Water/Oil/Water double emulsion/solvent evaporation, such as described for example in PCT patent application PCT/IB2017/053744 filed Jun. 22, 2017, the contents of which is hereby incorporated by reference in its entirety, with median size of the microcapsules being roughly 60 µm in diameter. The bacteriophage cocktail+polyvinyl alcohol (PVA) 1% (0.8 mL) was mixed with 13% PEAU (formulation #008) in DCM (8 mL) using high speed homogenizer for 15 s. The mixture was added drop-wise in cocktail+2% PVA (20 mL) while stirring DCM was allowed to evaporate overnight while stirring and beaker being capped with a glass watch. Final volume was 22-23 mL of Formulation 9. To prepare the Formulation 10, Formulation 9 was complemented with 3% PVA. Formulation 10 was stirred overnight at room temperature to ensure PVA is completely dissolved. Similarly, Formulation 11 was prepared by complementing Formulation 9 with 0.25 g/mL of Poloxamer P407. Formulation was stirred overnight at 4° C. to ensure P407 is completely dissolved Microcapsule solutions were dispensed in stoppered glass vials. Glass vials were uncapped and packaged in Tyvek™ pouches (4-5 samples/pouch), heat sealed between vials to isolate samples prior to their introduction into the reactor vessel and exposed to treatments 1 to 4 as previously described. Following treatment, the formulations are diluted 1/10 in TSB. 100ł of bacterial daily culture are added to 2.5 mL of TSB top agar (30 g/L TSB+0.7% agar). The mixture is poured on a TSA plate (30 g/L TSB+15% agar) immediately after brief vortex. 10 µL of each dilution are dispensed on the bacterial layer. Plates are incubated inverted at 37° C. for 18 hours. The plaques are counted in selected dilution (with 10-100 plaques) and the bacteriophage titer is calculated according to the following equation: bacteriophage titer=number of plaques*100/dilution factor. FIGS. 3, 4, and 5 demonstrate that the bacteriophage activity was maintained for all three formulations for 112 days when stored at 26° C. for accelerated stability.

TABLE 5

$scCO_2$ sterilization program.

| | Treatment 1 |
|---|---|
| Run time | 30 minutes |
| Pressurization/Depressurization times | 09:50/17:28 |
| Target temperature | 35° C. |
| Target pressure | 1,436 psi |
| Stirrer speed | 675 rpm |

Therefore, the proposed method not only preserves bacteriophage activity, but is able to result in products that have useful shelf life.

Example 6: Maintenance of Release Kinetics after Long Term Storage of Bacteriophages Containing Patches Patches prepared as in example 4 were stored for 18 months at either 4° C. or 26° C. to assess if the $scCO_2$ disinfection process affects the release of bacteriophages after long term storage. This test was performed to ensure that the disinfection process did not induce a pre-storage degradation of the polymer matrix or of the bacteriophages that would then be further damaged while in storage to a point where the progressive bacteriophage release characteristics of the polymer patches are unduly affected. To that effect, phage release was evaluated as stated in example 4, but instead of evaluating only total release, titration in the release medium was performed at various points over a week to evaluate the kinetics of the release.

Figure 6:
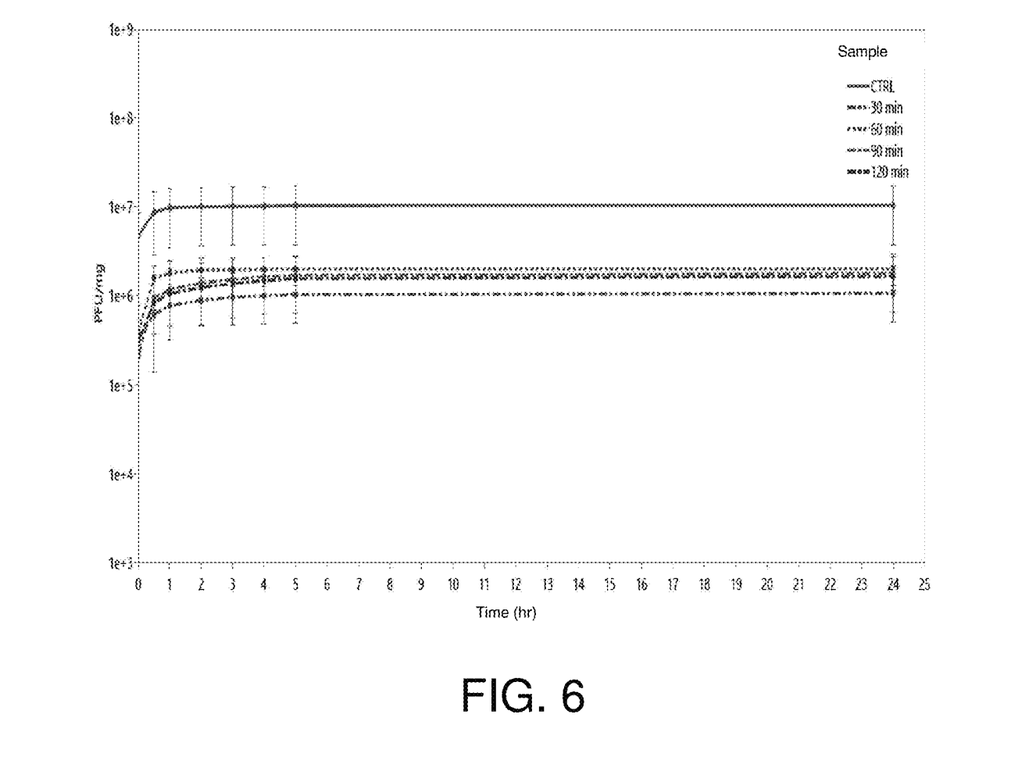
FIG. 6 illustrates the release of bacteriophages from polymer patches treated with $scCO_2$ as described in example 6 prior to storage of the patches.
Figure 7:
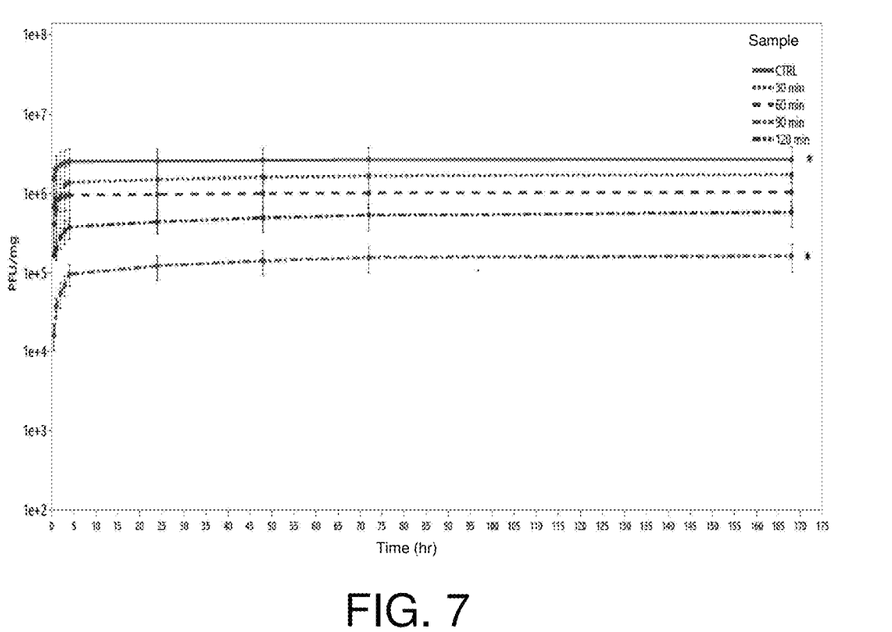
FIG. 7 illustrates the release of bacteriophages from polymer patches treated with $scCO_2$ as described in example 6 after storage for 18 months at 4° C.
Figure 8:
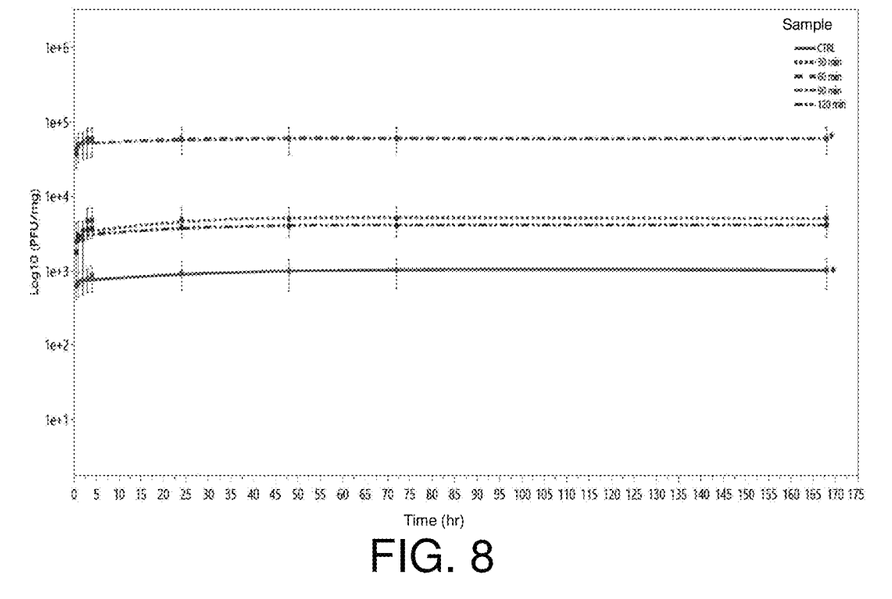
FIG. 8 illustrates the release of bacteriophages from polymer patches treated with $scCO_2$ as described in example 6 after storage for 18 months at 26° C.

FIG. 6 shows the phage titer in the incubation medium as a function of time prior to storage. The release kinetics is almost identical in disinfected (for 30, 60, 90 and 120 mins) and non-disinfected (CTRL) patches. Initial release (within 2 hours) is quick, followed by a stabilization after about 3 hours. Storage at 4° C. for 18 months (FIG. 7) did not affect significantly this kinetics in patches, whether they were subject or not to the $scCO_2$ treatment. There was still a significant release of bacteriophages from the patches even after 1 week (168 hours) of incubation. However, storage at 26° C. (FIG. 8) affected the patches and release is reduced by about 4 log after 18 months of storage (when compared to FIG. 6) and is also much smaller than release after storage at 4° C.

Although the present invention has been described hereinabove by way of exemplary embodiments thereof, it will be readily appreciated that many modifications are possible in the exemplary embodiments without materially departing from the novel teachings and advantages of this invention. Accordingly, the scope of the claims should not be limited by the exemplary embodiments, but should be given the broadest interpretation consistent with the description as a whole. The present invention can thus be modified without departing from the spirit and nature of the subject invention as defined in the appended claims.

What is claimed is:

1. A method for producing a disinfected product including bioactive bacteriophages infectious for predetermined bacteria, the disinfected product being usable in a target environment, the method comprising:

providing an initial product in which the bioactive bacteriophages are present in an initial quantity and protecting at least partially the bioactive bacteriophages from degradation by supercritical carbon dioxide ($scCO_2$) by at least one of lyophilizing the bioactive bacteriophages, immobilizing the bioactive bacteriophages on a polymer, and encapsulating the bioactive bacteriophages in microcapsules inside a hydrophobic layer to provide the bacteriophages in an anhydrous environment; and contacting the initial product with a disinfection fluid for a disinfection duration between 30 to 120 minutes under disinfection conditions to produce the disinfected product from the initial product, the disinfection fluid including $scCO_2$ at a pressure of between 8 MPa and 11 Mpa and wherein the disinfection fluid is at a temperature of between 31° C. and 38° C.;

wherein the bioactive bacteriophages are present in a final quantity in the disinfected product, the final quantity being effective for producing lysis of the predetermined bacteria to reduce bacterial content in the target environment when the disinfected product is used in the target environment;

wherein the polymer is selected from
(1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond,

(4) a poly (ester amide urethane) wherein at least one diol, at least one diacid, and at least one amino acid are linked together through an ester bond, an amide bond, and a urethane bond, (5) a poly (ester urea) wherein at least one diol and at least one amino acid are linked together through an ester bond and a urea bond, and (6) a poly (ester urethane) wherein at least one diol and at least one amino acid are linked together through an ester bond and a urethane bond, further wherein the at least one diol is a compound of formula:
HO—$R_1$—OH, $R_1$ is chosen from $C_2$-$C_{12}$ alkylene, alkylene interrupted by at least one oxygen, $C_3$-$C_8$ cycloalkylene, $C_3$-$C_{10}$ cycloalkylalkylene, the at least one diacid is a compound of formula:
HO—(CO)—$R_3$—(CO)—OH, $R_3$ is $C_2$-$C_{12}$ alkylene, the at least one amino acid is chosen from naturally occurring amino acids and non-naturally occurring amino acid.

2. The method as defined in claim 1, wherein the disinfected product is essentially free of bacterial contamination.

3. The method as defined in claim 1, wherein the disinfected product is essentially free of microorganisms.

4. The method as defined in claim 1, wherein protecting the bioactive bacteriophages includes immobilizing the bioactive bacteriophages on a polymer.

5. The method as defined in claim 1, wherein the polymer is a poly (ester amide urea) comprising the following two blocks with random distribution thereof:

wherein
the ratio of l:m ranges from 0.05:0.95 to 0.95:0.05, l+m=1, $R_1$ is chosen from $C_2$-$C_{12}$ alkylenes optionally interrupted by at least one oxygen, $C_3$-$C_8$ cycloalkylenes, $C_3$-$C_{10}$ cycloalkylalkylenes, $R_3$ is $C_2$-$C_{12}$ alkylene, $R_2$ and $R_4$ are independently chosen from the side chains of L- and D-amino acids so that the carbon to which $R_2$ or $R_4$ is attached has L or D chirality.

6. The method according to claim 5, wherein $R_1$ is —$(CH_2)_6$—, $R_3$ is —$(CH_2)_8$— and both $R_2$ and $R_4$ are the side chain of L-leucine.

7. The method as defined in claim 1, wherein the disinfection fluid includes at least 99.9% of $scCO_2$.

8. The method as defined in claim 1, wherein the disinfection fluid is substantially free of water.

9. The method as defined in claim 1, wherein the disinfection fluid further comprises a sterilant additive suitable for increasing $CO_2$ penetration through bacterial cellular membranes in addition to $scCO_2$.

10. The method as defined in claim 9, wherein the sterilant additive is selected from the group consisting of acetic acid, tert-butyl hydroxy peroxide, paracetic acid, ethanol, formic acid and hydrogen peroxide.

11. The method according to claim 9, wherein the disinfection fluid includes between about 0.2% to about 10% of the sterilant additive per volume.

12. The method as defined in claim 1, wherein the method reduces a phage titre of the bioactive bacteriophage in a bacteriophage containing portion of the initial product by at most a factor of 100 so that the final quantity is at least 1 percent of the initial quantity.

13. A method of eliminating or reducing bacterial contamination of a product including a bacteriophage containing composition, the method comprising exposing the product to supercritical $CO_2$ ($scCO_2$), wherein the bacteriophage containing composition includes bioactive bacteriophages after exposition to $scCO_2$, further wherein the bacteriophage containing composition includes at least one of bacteriophages dispersed in a polymer and bacteriophages immobilized on a polymer to provide the bacteriophages in an anhydrous environment and the bacteriophage containing composition is treated with scCO$_2$ at between about 9 MPa and about 10 MPa at between about 31° C. and about 38° C., and for between about 30 min and about 120 min;
wherein the polymer is selected from
(1) a poly (ester amide urea) wherein at least one diol, at least one diacid, and at least one amino acid are linked together through an ester bond, an amide bond and a urea bond,
(2) a poly (ester urethane urea) wherein at least one diol and at least one amino acid are linked together through an ester bond, a urethane bond, and a urea bond,
(3) a poly (ester amide urethane urea) wherein at least one diol, at least one diacid, and at least one amino acid are linked together through an ester bond, an amide bond, a urethane bond, and a urea bond,
(4) a poly (ester amide urethane) wherein at least one diol, at least one diacid, and at least one amino acid are linked together through an ester bond, an amide bond, and a urethane bond,
(5) a poly (ester urea) wherein at least one diol and at least one amino acid are linked together through an ester bond and a urea bond, and
(6) a poly (ester urethane) wherein at least one diol and at least one amino acid are linked together through an ester bond and a urethane bond,
further wherein
the at least one diol is a compound of formula:
HO—R$_1$—OH, R$_1$ is chosen from C$_2$-C$_{12}$ alkylene, alkylene interrupted by at least one oxygen, C$_3$-C$_8$ cycloalkylene, C$_3$-C$_{10}$ cycloalkylalkylene, , and

, the at least one diacid is a compound of formula:
HO—(CO)—R$_3$—(CO)—OH, R$_3$ is C$_2$-C$_{12}$ alkylene,
the at least one amino acid is chosen from naturally occurring amino acids and non-naturally occurring amino acid.

14. The method as defined in claim 13, wherein the bacteriophage containing composition includes bacteriophages adsorbed, adhered or otherwise immobilized on a surface, the product being an implant for implantation in a human or animal body, the surface being an exposed surface of the implant.

15. The method as defined in claim 13, wherein the bacteriophage containing composition is treated with a sterilant additive in addition to scCO$_2$, the sterilant additive being suitable for increasing CO2 penetration through bacterial cellular membranes.

16. The method as defined in claim 15, wherein the sterilant additive is selected from the group consisting of acetic acid, tert-butyl hydroxy peroxide, paracetic acid, ethanol, formic acid and hydrogen peroxide.

17. A disinfected product obtained by the method according to claim 1, the disinfected product being usable in a target environment for controlling growth of predetermined bacteria in the target environment, the disinfected product comprising: bioactive bacteriophages infectious for the predetermined bacteria.

18. The disinfected product according to claim 17, wherein the disinfected product is essentially free of bacterial contamination.

19. The disinfected product according to claim 17, wherein the disinfected product is selected from the group consisting of a polymer patch, a suspension of polymer microcapsules, an implant including a surface coated with a polymer and a powder composition including lyophilized bacteriophages.

20. The method as defined in claim 1, further comprising drying the initial product before contact with the disinfection fluid.

* * * * *